United States Patent [19]
Frechette et al.

[11] Patent Number: 5,707,990
[45] Date of Patent: Jan. 13, 1998

[54] 2-SUBSTITUTED AMINO AND THIO ALKYL BENZOXAZINE ANTIMICROBIAL AGENTS

[75] Inventors: Roger Frechette; Michael Beach, both of Somerville, N.J.

[73] Assignee: Ortho Pharmaceutical Corporation, Raritan, N.J.

[21] Appl. No.: 594,020

[22] Filed: Jan. 30, 1996

[51] Int. Cl.$^6$ .................. A61K 31/535; C07D 265/36
[52] U.S. Cl. ........................... 514/230.5; 544/105
[58] Field of Search ................. 544/105, 230.05

[56] References Cited

PUBLICATIONS

M. J. Mahan, J. M. Slauch and J. J. Mekalanos, Science vol. 259, 686–688 (1993) Selection of Bacterial Virulence Genes that are Specifically Induced in Host Tissues.

S. Roychoudhury et al., Proc. Nat. Acad. Sci., vol. 90, 965–969 (1993) Inhibitors of Two–Component Signal Transduction Systems: Inhibition of Alginate Gene Activation in *Pseudomonas Aeruginosa*.

Kajino, Chemical Abstract 116:174105 for Chem. Pharm. Bull, 39(11), 2896–905 (1991).

Meguro, Chem. Abstract 108:37848 for EP–233,728 (Aug. 26, 1987).

Masuoka et al, Chem. Pharm. Bull, 34(1), pp. 130–139 (1986).

*Primary Examiner*—Philip I. Datlow
*Attorney, Agent, or Firm*—Kenneth J. Dow

[57] ABSTRACT

The invention relates to benzoxazine and pyrido-oxazine antibacterial compounds of the general formula:

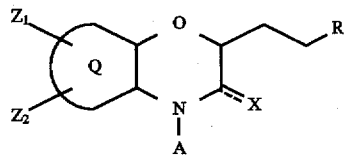

wherein the moiety Q is a fused phenyl or fused pyridyl moiety and R is a substituted amine or substituted thio moiety as herein described, pharmaceutical compositions containing the compounds, methods for their production and their use in treating bacterial infections.

13 Claims, No Drawings

2-SUBSTITUTED AMINO AND THIO ALKYL BENZOXAZINE ANTIMICROBIAL AGENTS

FIELD OF THE INVENTION

The invention relates to benzoxazine and pyrido-oxazine antibacterial compounds, pharmaceutical compositions containing the compounds, and methods for their production and use. These compounds are effective in inhibiting the action of a bacterial histidine protein kinase and are thus useful as anti-infective agents against a variety of bacterial organisms, including organisms which are resistant to other known antibiotics.

BACKGROUND OF THE INVENTION

Prokaryotes regulate the transcription of many of their genes in response to changes in the organisms' environment (J. B. Stock, A. M. Stock, and J. M. Mottonen, *Nature*, 344, 395–400 (1990)). Such regulation is essential if the organism is to adapt itself to survival in a changing environment, and pathogenic bacteria rely on such regulatory systems to enable them to survive within their host's body (J. F. Miller, J. J. Mekalanos, S. Falkow, *Science*, 243, 1059 (1989)). Chemical compounds that interfere with the regulatory mechanisms would be expected to be useful anti-infective drugs, as they would prevent bacteria from making necessary adaptive changes in their patterns of gene expression.

Virulence, chemotaxis, toxin production, sporulation, and reproduction are examples of the bacterial processes that are under regulatory control, and which could be inhibited by such compounds. The inhibition of one or more of these processes is expected to lead to reduced virulence, a slowing or halting of bacterial growth and reproduction, and even to bacterial cell death if vital functions are interrupted.

For example, it has been shown that Salmonella species express certain proteins, under regulatory control and in response to the presence of intestinal epithelial cells, which enable them to adhere to and invade these cells. Bacteria unable to synthesize these proteins are avirulent: they cannot cause infection in mice (B. B. Finlay, F. Heffron, S. Falkow, *Science*, 243, 940–943 (1989)). A similar effect would be expected if the genes coding for these proteins were intact, but remained unexpressed.

To accomplish adaptive responses to the environment, bacteria rely on phosphorelay mechanisms, referred to in the art as "two-component switches." These switches have the net effect of transmitting information from the environment to the cell nucleus, where the information is responded to by the switching on or off of transcription of relevant genes. The first step of this phosphorelay scheme relies on numerous histidine protein kinase (HPK) enzymes. Most of these HPK enzymes are sensor molecules, and respond to stimulation by specific environmental signals by transferring phosphate from ATP to a histidine residue of the HPK protein. Some HPK enzymes are stimulated by the presence of acceptor proteins (described below), the concentration of which are modulated by environmental signals. In either case, this auto-phosphorylation is followed by transfer of the phosphate to an aspartyl residue of one or more acceptor proteins (the second components of the two-component switch), which are either regulators of gene expression (by binding to control regions on DNA, or to the RNA polymerase complex) or are themselves kinases for other acceptor molecules. These secondary acceptors may again be regulatory proteins, or kinases toward yet another protein. This cascade of phosphate from protein to protein eventually results in the phosphorylation of one or more regulatory proteins, which then control gene expression.

Mammalian cells do not, or at least are not presently known to, utilize HPK-driven phosphorelay systems for gene regulation. Thus, compounds which selectively inhibit either the autophosphorylation of the HPK protein, or the phosphotransfer step(s), or both, would not be expected to have undesirable effects on the host organism, and are promising candidates for antiinfective drugs. The emergence of drug-resistant pathogenic organisms that are resistant to one or more of the currently available drugs has created a need for novel antibiotics, that act by mechanisms unrelated to those of currently available agents, and inhibitors of HPK would fill this need. The presence of multiple HPK-driven systems (over fifty are currently known) in bacteria gives HPK inhibitors a potential advantage over current antibiotics, in that mutations of a single HPK enzyme are unlikely to confer drug resistance to an organism.

Recently, workers in this field reported a method for detecting bacterial "virulence" genes that are selectively expressed when bacteria infect a host (M. J. Mahan, J. M. Slauch, and J. J. Mekalanos, *Science*, 259, 686–688 (1993)). The potential use of this information in the design of new antibiotics was mentioned, but actual methods of reducing expression of these genes were not described. A preliminary report from another group of workers disclosed inhibitors of the two-component switch controlling alginate gene activation in *Pseudomonas aeruginosa* in an in vitro system (S. Roychoudhury et al., *Proc. Nat. Acad. Sci.*, 90, 965–969 (1993)), but no anti-bacterial activity of the compounds was reported.

SUMMARY OF THE INVENTION

The invention comprises compounds of general structure 1 shown below:

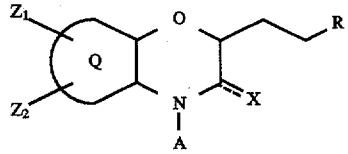

wherein the moiety Q is a fused phenyl or fused pyridyl moiety;

$Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or a halogen;

X is hydrogen or oxygen;

A is $C_1$–$C_6$ alkyl, $C_1$–$C_6$ alkylaryl or $C_1$–$C_6$ alkylheterocyclyl wherein aryl is biphenyl, naphthyl or phenyl; and heterocyclyl is a 5 or 6 membered saturated or unsaturated heterocyclic group containing 1–4 nitrogen atoms, an oxygen or a sulfur atom;

wherein said aryl or heterocyclyl group is optionally substituted with ($C_1$–$C_6$)alkyl, benzyl, oxybenzyl, phenoxy, hydroxy, alkoxy, halogen, dihalogen, nitro, amino, carboxyl, carbo($C_1$–$C_4$)alkoxy or methylsulfonylamino;

R is a moiety selected from:

(a) $NHR_1R_2$, $N^+R_1R_2R_3$;

(b) 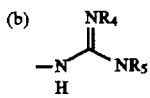

(c) a moiety selected from:

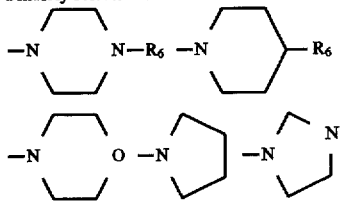

(d) a moiety selected from:

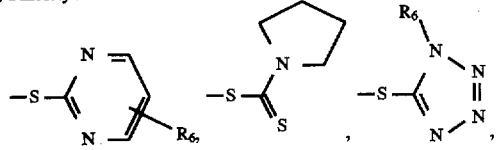

(e) $C(O)NH(C_1-C_3)NH(C_1-C_6)NH_2$;

wherein $R_1$, $R_2$ and $R_3$ are independently hydrogen, $C_1-C_6$ alkyl, t-butoxycarbonyl, or carboxyethylpiperidine;

$R_4$ and $R_5$ are independently t-butoxycarbonyl or hydrogen or $R_4$ and $R_5$ may be joined together to form an imidazoline, imidazolyl or pyrimidine ring; and $R_6$ is hydrogen, $C_1-C_6$ alkyl, acyl, phenyl, or substituted phenyl wherein the substituent is halogen, or methylbenzyldioxolane;

and the pharmaceutically acceptable salts, esters and prodrug forms thereof.

Another aspect of the invention comprises a method of treating bacterial infections in mammals by administering to a mammal suffering from such infection a therapeutically effective amount of a compound selected from those of Formula 1 effective in inhibiting the action of a bacterial histidine protein kinase.

The compounds of the present invention inhibit the autophosphorylation of bacterial histidine kinases; they also inhibit the transfer of phosphate from phosphorylated histidine kinases to the aspartyl residues of the phosphate acceptor proteins involved in regulation of bacterial gene expression. The compounds are useful as bacteriostatic and bactericidal agents, and as anti-infective agents in the treatment of infectious diseases. They may also have utility in increasing the sensitivity of bacteria to conventional antibiotics.

DETAILED DESCRIPTION

Relative to the above generic description, certain compounds of formula 1 are preferred.

Preferred embodiments are those compounds wherein Q is fused phenyl.

Preferred groups for A are $C_1-C_5$ alkyl, $CH_2$phenyl, $CH_2$thienyl, $CH_2$pyridyl, $CH_2$furyl, or ethyl piperidine.

Preferred groups for R are:

(a) $NHR_1R_2$, $N^+R_1R_2R_3$;

(b) 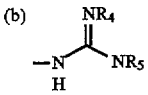

(c) a moiety selected from:

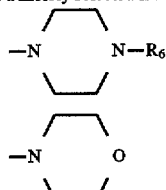

(d) a moiety selected from:

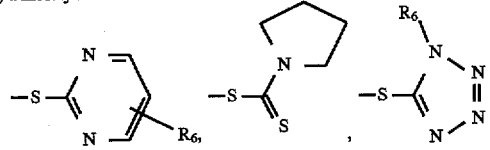

(e) $C(O)NH(C_1-C_3)NH(C_1-C_6)NH_2$;

wherein $R_1$, $R_2$ and $R_3$ are independently hydrogen, $C_1-C_6$ alkyl, t-butoxycarbonyl or carboxyethylpiperidine;

$R_4$ and $R_5$ are independently t-butoxycarbonyl or hydrogen;

$R_6$ is hydrogen, $C_1-C_6$ alkyl, acyl, phenyl, or substituted phenyl wherein the substituent is halogen or methylbenzyldioxolane.

Most preferred are those compounds of formula 1 wherein: the moiety Q is a fused phenyl;

$Z_1$ is hydrogen, halogen, $C_1-C_6$ alkyl, $C_1-C_6$ alkoxy, phenyl, hydroxy, amino, nitro, sulfonylamino or trifluoromethyl;

$Z_2$ is hydrogen or, where $Z_1$ is a halogen, $Z_2$ is also a halogen;

X is oxygen;

A is $C_1-C_5$ alkyl, $CH_2$phenyl, $CH_2$thienyl, $CH_2$pyridyl, $CH_2$furyl, or ethyl piperidine; wherein said phenyl, thienyl, pyridyl, furyl or piperidine moiety is optionally substituted with ($C_1-C_6$)alkyl, benzyl, oxybenzyl, phenoxy, hydroxy, alkoxy, halogen, dihalogen, nitro, amino, carboxyl or carbomethoxy;

R is a moiety selected from:

(a) 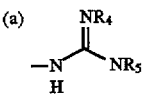

(b) a moiety selected from:

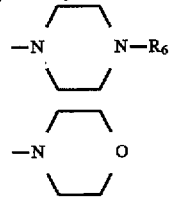

(c) a moiety selected from:

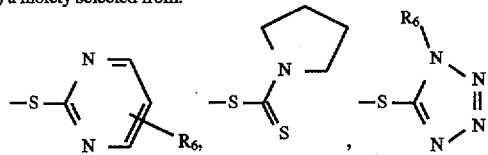

wherein $R_4$ and $R_5$ are independently t-butoxycarbonyl or hydrogen;

$R_6$ is hydrogen, $C_1$–$C_6$ alkyl, acyl, phenyl, or substituted phenyl wherein the substituent is halogen or methylbenzyldioxolane and the pharmaceutically acceptable salts, esters and prodrug forms thereof.

In another aspect of the present invention, certain novel intermediates useful in the preparation of the final compounds are contemplated. Thus the invention encompasses intermediates of the following formula:

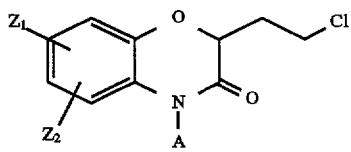

wherein $Z_1$, $Z_2$, and A are as described above.

The compounds of the present invention are prepared in accordance with the methods described below and illustrated in the following Schemes. The first step in the synthesis involves a novel addition, cyclization reaction of the α-bromo-γ-butyrolactone shown in Scheme 1 with a suitably substituted 2-nitro or 2-aminophenol. The reaction may be carried out in two discrete steps, beginning with known, generally commercially available nitrophenols having most of the definitions for Z cited in the invention description. The solvent is usually DMF and a basic reagent such as $K_2CO_3$ is needed to drive the reaction to completion. The cyclization step occurs upon reduction of the nitro group with any of the reagent systems known to be useful for this reduction, including palladium catalyzed hydrogenation, nickel and sodium borohydride, and iron-acetic acid. Alternatively, especially in cases where Z is a nitro group or Q is a fused pyridyl, both the addition and cyclization steps may be carried out in a single procedure, with a suitably substituted aromatic amine, using a base, such as $K_2CO_3$ or NaH, in DMF with or without heating.

Having generated the benzoxazine heterocyclic ring system in this manner, the intermediate alcohol 2 may be prepared by a three step sequence of reactions. Protection of the alcohol group, with a known protecting group such as a t-butyldimethylsilyl derivative or equivalents thereof, is followed by reaction at the 4-position involving nucleophilic displacement of an alkyl or aryl halide under basic conditions: for example, NaH in DMF is highly effective. Alternatively, derivatization of the 4-position nitrogen may be carried out by Mitsunobu reaction of a suitably substituted alcohol. Deprotection of the alcohol with any of the usual fluoride anion reagents or under acidic conditions provides compound 2.

As is apparent, Scheme 1 depicts the preparation of benzoxazine compounds wherein the "Q" moiety is a fused phenyl. The pyrido-oxazine compounds where the "Q" moiety is a fused pyridyl may be prepared in accordance with the same procedure by using a suitably substituted 2-nitro- or 2-amino pyridoxyl moiety in place of the phenol starting material depicted in Scheme 1. In the remaining synthesis depicted in Schemes 2–10 hereinafter, the pyrido-oxazine compounds may likewise be conveniently substituted for the benzoxazine compounds illustrated in the Schemes.

Scheme 1

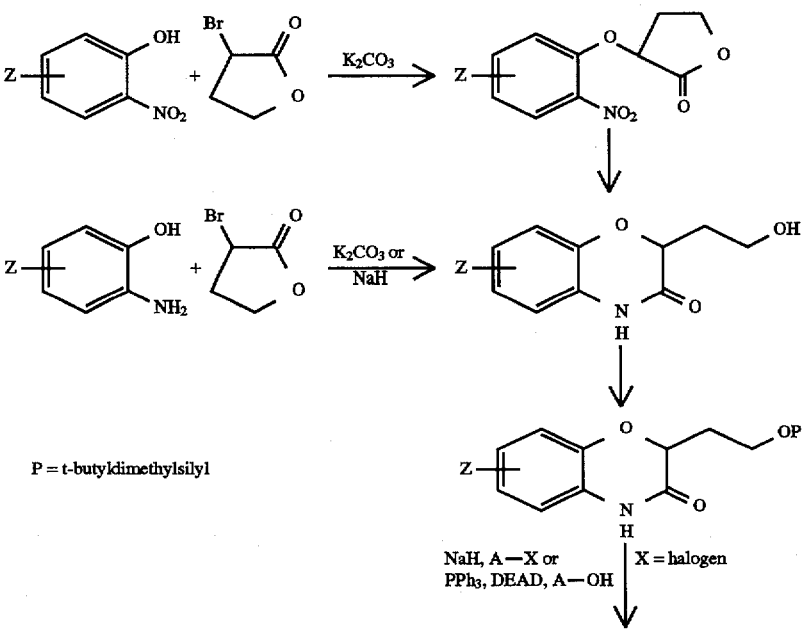

P = t-butyldimethylsilyl

-continued
Scheme 1

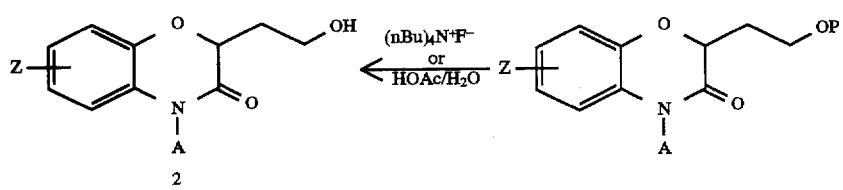

For preparation of the compounds where R is an amino derivative, as shown in Scheme 2, the alcohol 2 is converted to the halide derivative 3 by reaction with an appropriate halogenating agent such as carbon tetrachloride in the presence of an appropriate phosphine reagent, such as trioctylphosphine or the like in a suitable solvent. The halide derivative is then subjected to nucleophilic displacement conditions with the amino derivative HNR', wherein R', together with the nitrogen to which it is attached, is any of the amino derivatives of R above, in a polar, aprotic solvent, such as DMF, at room temperature, to yield compound 4.

Scheme 2

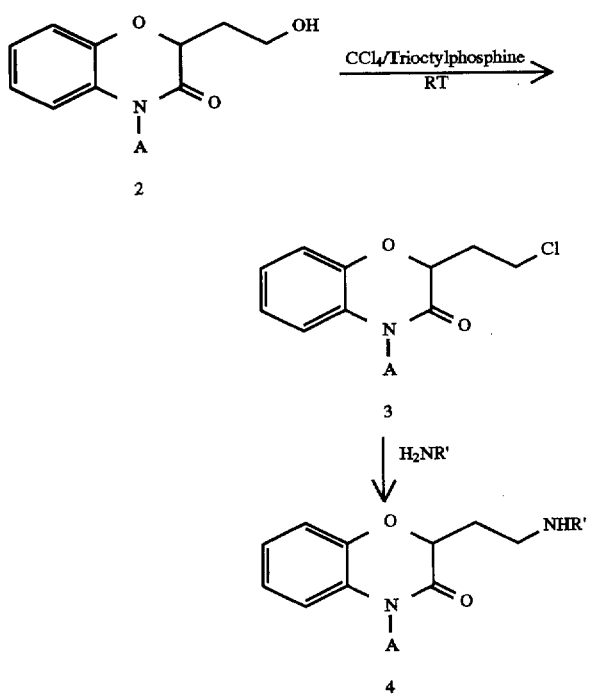

Likewise, the substituted thiol compounds are prepared in accordance with Scheme 3 by nucleophilic displacement of the halide with a thiolate, such as NaSR" or $NH_4SR$", wherein R", together with the sulfur to which it is attached, is any of the thiol derivatives of R above, to yield the sulfides 5.

Scheme 3

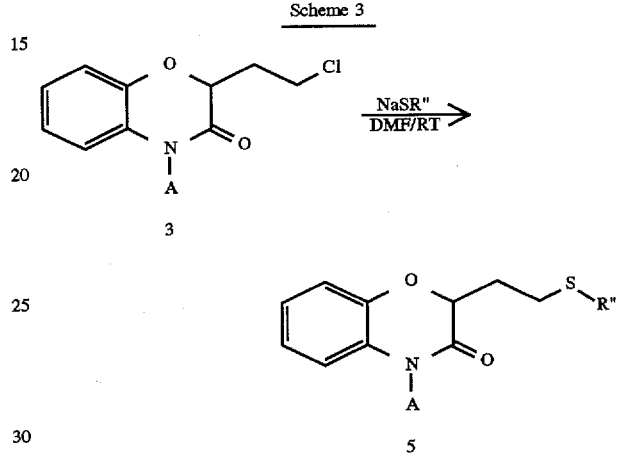

For preparation of the guanidine derivatives, the key step of the synthesis is a Mitsunobu reaction of the alcohol 2 with a protected guanidine such as the bis-boc protected guanidine, as shown in Scheme 4. Suitable protecting groups for guanidines include, but are not limited to, trifluoroacetyl, t-butoxycarbonyl (Boc), and benzyloxycarbonyl. The Mitsunobu reaction may be one of several variants known in the art; the selection of the appropriate phosphine, azodicarbonyl reagent, and solvent will be at the discretion of the practitioner, based on published precedents and on empirical results with the particular combination of substrates to be coupled. Guidance can be found in the review article by D. L. Hughes, in *Organic Reactions*, 42, 335–656 (1992), and in the detailed examples below. In most cases triphenylphosphine ($Ph_3P$) and diethylazodicarboxylate (DEAD), or alternatively tributylphosphine ($Bu_3P$) and (azodicarbonyl) dipiperidine (ADDP), will suffice. Deprotection of the guanidine is conveniently carried out by treatment with an acid such as, for example, trifluoroacetic acid in methylene chloride or hydrochloric acid in isopropanol, followed by routine purification methods, as needed.

Scheme 4

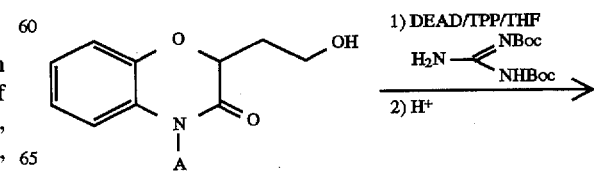

Scheme 4

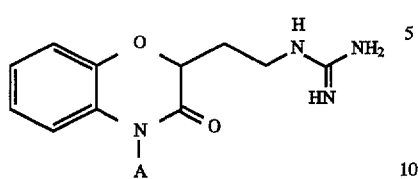

In the cases where A (see description of invention), is a carboxylic acid substituted benzyl group, the alcohol shown in Scheme 5 may be prepared by the method outlined in Scheme 1, using known benzylic halides bearing a carboxylic ester substituent. The previously described transformations are carried out with the ester in place, followed by hydrolysis of the ester to generate the acid, usually in the final step of the sequence.

Scheme 5

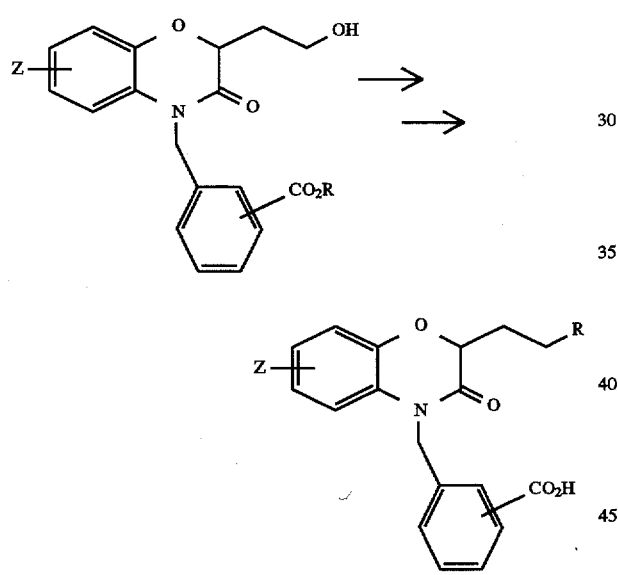

The transformations outlined in Scheme 1, for preparation of alcohol 2 and the coupling reaction described in Scheme 2 may be carried out on nitro substituted starting materials to afford the products shown in Scheme 6. Reduction of the nitro group with reagents such as iron/acetic acid or palladium catalyzed hydrogenation, can be carried out on, for example, compounds wherein R is a protected amino or guanidine moiety. Alternatively, the reduction may be effected on the unprotected compounds, provided that no further manipulations are needed. With the protected species, the resulting amine may be further functionalized with electrophilic reagents to afford the products shown in Scheme 6. Similar transformations can be carried out on compounds derived from 2 bearing a nitrobenzyl substituent, as shown in Scheme 7.

Scheme 6

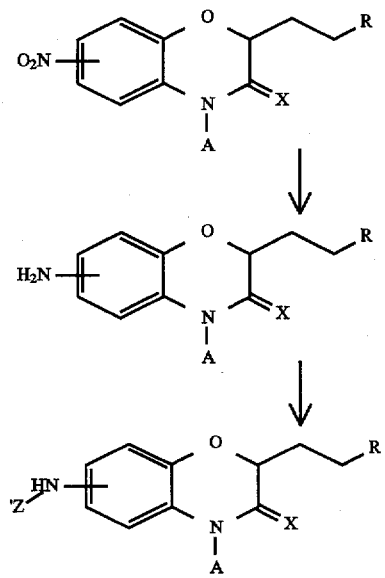

$Z' = SO_2R_{10}, COR_{10}$
$R_{10} = $ alkyl, aryl

Scheme 7

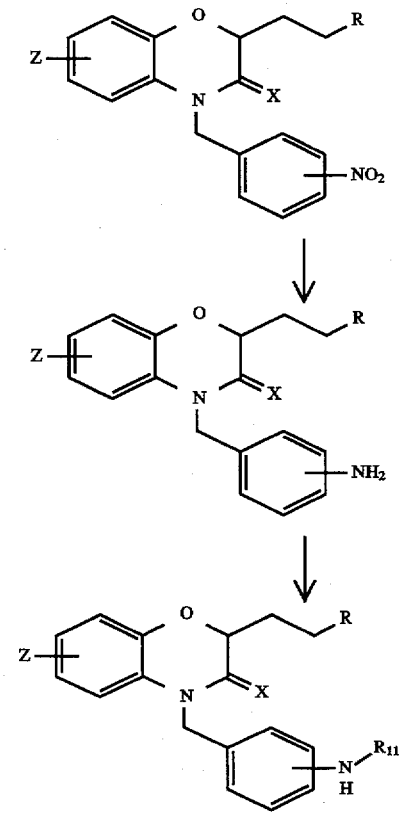

$R_{11} = SO_2R_{12}, COR_{12}$
$R_{12} = $ alkyl, aryl

The foregoing reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgment as to the order of synthetic steps, protection of reactive groups, and selection of reaction conditions. Reaction conditions compatible with the substituents employed will be apparent to one skilled in the art, as will be the selection of protecting groups where needed.

From formula 1 it is evident that some of the compounds of the invention may have one or more asymmetrical carbon atoms in their structure. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereospecific reactions.

Suitable pharmaceutical salts are those of inorganic or organic acids, such as hydrochloric acid, hydrobromic acid, hydroiodic acid, sulfuric acid, nitric acid, phosphoric acid, acetic acid, succinic acid, oxalic acid, malic acid and the like. Suitable salts are also those of inorganic or organic bases, such as KOH, NaOH, $Ca(OH)_2$, $Al(OH)_3$, piperidine, morpholine, ethylamine, triethylamine and the like.

Also included within the scope of the invention are the hydrated forms of the compounds which contain various amounts of water, for instance, the hydrate, hemihydrate and sesquihydrate forms.

The ability of bacteria to quickly respond to changes in the environment is of utmost importance for their survival. Bacteria are capable of rapidly responding and adapting to such diverse stimuli as changes in nutrients, osmolarity, temperature, light, or host environment. These responses may be transient, such as those required for changes in motility or for entry into a host cell. Alternatively, the responses may require major shifts in gene expression and cell morphology, such as those required for sporulation, or for survival within a macrophage. The mechanism by which bacteria are able to sense cues from the physical environment (or from within the cytoplasm) and process these signals into appropriate responses often involves the so-called "two-component" systems.

As stated above, the treatment method of the present invention is based on the inhibition of this "two-component switch" system. All bacteria use this mechanism to control various adaptive/virulence factors to facilitate establishment of a bacterial population in the environment (for example, a bacterial infection in a host). The system invariably consists of a sensor which either activates a kinase or is a part of the kinase, and which upon stimulation, autophosphorylates. This phosphorylated species is a highly active phosphodonor which immediately transfers its phosphate to a "regulatory" component, which in turn initiates the biological response such as transcription or further phosphotransfer in a cascade which eventually ends in regulation of bacterial gene expression. Although each of the kinases and response regulators has a unique sequence (in fact, even functionally identical proteins have slightly different sequences in different species) they share a homologous biochemical mechanism and they share significant homology in the active site.

As stated, the present invention provides compounds which exhibit antibiotic activity by inhibiting the autophosphorylation of bacterial histidine kinases. They also inhibit the transfer of phosphate from phosphorylated histidine kinases to the aspartyl residues of the phosphate acceptor proteins involved in regulation of bacterial gene expression.

This invention further provides a method of treating bacterial infections, or enhancing or potentiating the activity of other antibacterial agents, in warm-blooded animals, which comprises administering to the animals a compound of the invention alone or in admixture with another antibacterial agent in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacological acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given in divided doses two to four times a day, or in sustained release form. For most large mammals the total daily dosage is from about 0.07 g to 7.0 g, preferably from about 100 mg to 1000 mg. Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

The compounds of the present invention have antibacterial activity as determined by the following tests. First, the compounds were tested for their activity in inhibiting the autophosphorylation of Kinase A and the transphosphorylation of SpoOF, two proteins involved in one of the above described signal transduction systems controlling gene expression in bacteria. Representative compounds were then tested for antibacterial activity against selected organisms by the standard MIC method. The results are set forth below.

Table 1 lists examples of compounds of the invention, along with their $IC_{50}$ values in the HPK in vitro assay described below. These examples are merely illustrative of the invention, and are not intended to limit the scope of the claims in any way. In Table 1, benzoxazine compounds are listed in accordance with the following formula:

TABLE 1

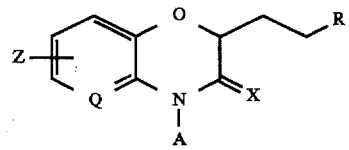

KEY: Bz = benzyl

| Ex. # | A | Z | X | Q | R | $IC_{50}(\mu M)$ |
|---|---|---|---|---|---|---|
| 18 | 3-ClBz | 6-CF$_3$ | O | CH | HN–C(=NH)–NH$_2$ | 80 |
| 19 | 3-ClBz | 6-CH$_3$ | O | CH | HN–C(=NH)–NH$_2$ | 52 |
| 20 | 3-ClBz | H | O | N | HN–C(=NH)–NH$_2$ | 344 |
| 21 | 3-NO$_2$Bz | H | O | CH | HN–C(=NH)–NH$_2$ | 621 |
| 22 | 2-ClBz | H | O | CH | HN–C(=NH)–NH$_2$ | 325 |
| 23 | 3-ClBz | 7-NO$_2$ | O | CH | HN–C(=NH)–NH$_2$ | 182 |
| 24 | 2-ClBz | H | O | CH | S–(tetrazole) | 999 |

TABLE 1-continued

[Structure: Z-substituted ring with O, Q, N-A, X=, with R group chain]

KEY: Bz = benzyl

| Ex. # | A | Z | X | Q | R | $IC_{50}(\mu M)$ |
|---|---|---|---|---|---|---|
| 25 | 2-ClBz | H | O | CH | S—C(=S)—N(pyrrolidine) | 274 |
| 26 | 2-ClBz | H | O | CH | S—C(=N)—(pyrimidine-like N=) | 999 |
| 27 | 2-ClBz | H | O | CH | piperazine-N-CH₂-phenyl | 1000 |
| 28 | 2-ClBz | H | O | CH | piperazine-N-(4-F-phenyl) | 999 |
| 29 | 3-ClBz | H | O | CH | HN-C(=O)-...-NH-...-NH₂ (polyamine chain) | 852 |

The protocol for the above referenced assay is as follows.

Autophosphorylation of Kinase A and Transphosphorylation of SpoOF Assay

To study the effect of the compounds of the present invention on the signal transduction process in bacteria, the inhibiting effect of the compounds on the sporulation operon proteins Kinase A and SpoOF was examined. Specifically, the inhibition of autophosphorylation of Kinase A and the transphosphorylation of SpoOF was determined in the following assays. The SpoOF response regulator is the primary substrate for phosphorylation by the protein kinase, Kin A, involved in the sporulation process in bacteria. See D. Burbulys, K. A. Trach, J. A. Hoch, Cell, 64, 545–552 (1991). SpoOF and KinA were prepared from recombinant E. coli overexpressing the proteins (J. Cavanagh et al, Amino Adds, 6, 131–140 (1994) and references therein).

The following stock reagents were either prepared and used promptly or stored at the indicated temperature:

8 X Salts: 2M KCl (5 mL), 1M $MgCl_2$ (800 mL), 1M $CaCl_2$ (100 mL), 10 mg/mL phenylmethylsulfonyl fluoride (200 mL), 1M dithioreitol (50 mL), 0.25M $Na_2EDTA$ (32 mL) and $H_2O$ 3.82 mL (–20° C.)

5X Loading Dye: 0.5M TRIS-HCl-pH 6.8 (7.5 mL), 10% SDS (2 mL) 0.1% bromophenol blue (0.5 mL), 100% glycerol (3 mL) and 12.5M 2-mercaptoethanol (0.3 mL)

1–1.3 mg/mL KinA: 15 mM TRIS-HCl, pH 8.0, 6 mM KCl; 4 mM 2-mercaptoethanol; 40% glycerol (–20° C.)

1 mg/mL SpoOF: 17.5 mM TRIS-HCl, pH 8.0; 0.7 mM KCl; 0.7 mM $MgCl_2$; 0.7 mM $CaCl_2$; 5 mM 2-mercaptoethanol; 30% Glycerol (–20° C.)

5% Stacking Gel: 40% 29:1 acrylamide:bis acrylamide (1.25 mL), 0.5M TRIS-HCl, pH 6.8 (2.5 mL), 10% SDS (0.1 mL), D-$H_2O$ (6.15 mL) 10% ammonium persulfate (100 mL) and TEMED (25 mL)

SDS Running Buffer: TRIS-BASE (3.02 g), glycine (14.4 g) SDS (1 g), D-$H_2O$ (to 1 L)

The reaction mixture was prepared from 8X Salts (87 μL), 1M TRIS, pH 8 (118 μL), 50% glycerol (63 μL), SpoOF (14.1 μL) and KinA (7.0 μL). Microcentrifuge tubes were charged with the reaction mixture (18.5 μL) and a 1.0 mM solution of the test compound in 5% DMSO (18.5 μL), and incubated for 15 min on ice. 100 mM ATP solution (3.0 μl, containing 625 μCi [$^{32}$P]ATP) was added, and the mixture left for 10 minutes at room temperature. The reaction was quenched with 5X loading dye (10 μL per tube) and the samples were loaded on a prepared 5% Stacking Gel, or stored on dry ice until ready for use. The prepared wells were filled with SDS Running Buffer, samples were loaded into the wells, and 80 volts were applied to the gel until the dye front reached the bottom of the stacking gel. The voltage was then increased to 250 volts until electrophoresis was complete. Radioactive bands in the gel corresponding to phosphorylated KinA and SpoOF were imaged and quantitated with a phosphoimager.

If either enzyme was inhibited (as evidenced by the absence of labelled protein in the developed gel), an IC$_{50}$ was calculated by running the assay with a range of inhibitor concentrations from 1 to 500 μM. After electrophoresis of the reaction mixtures, percent inhibition was determined by measuring the concentration of radioactive phosphorus with a phosphoimager and calculating the values using a software program (BioRad Molecular Analyst). IC$_{50}$ values of less than 1000 μM are considered active.

The following examples describe in detail the chemical synthesis of representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

Methods of preparing the exemplified compounds of the invention are presented below. These examples are intended to illustrate the methods of synthesis, and are not intended to limit the scope of the claims in any way. Abbreviations used: DEAD, diethyl azodicarboxylate; Ph$_3$P, triphenylphosphine; THF, tetrahydrofuran; DMF, N,N-dimethylformamide;

EXAMPLES

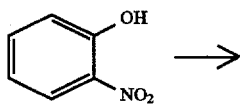

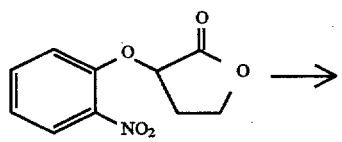

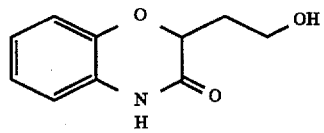

Method A: 2-Hydroxynitrobenzene (20.2 g, 1 eq) was dissolved in DMF (250 ml) and treated with K$_2$CO$_3$ (30 g, 1.3 eq), followed by addition of α-bromo-γ-butyrolactone (14.4 ml, 1.2 eq) at room temperature under nitrogen. After stirring 18 h, an additional amount of K$_2$CO$_3$ (5g, 0.25 eq) was added. After a total reaction time of 48 h, the reaction was cooled in an ice bath and acetic acid (13.7 ml, 1.65 eq) was added. The crude reaction mixture was poured into water and extracted with EtOAc. The combined extract was concentrated under vacuum and crystallized from ethanol/water to afford the phenoxyfuranone as white needles.

The phenoxy furanone (11.9 g, 1 eq) was reacted with H$_2$ at 50 psi in a Parr shaker bottle containing 10% Pd/C (1.8 g, 15% w/w) in EtOH (200 ml) for 13 h. The catalyst was removed by filtration and the filtrate concentrated under vacuum. The crude product was triturated with hot Et$_2$O to afford the benzoxazinone in 87% yield as a white powder.

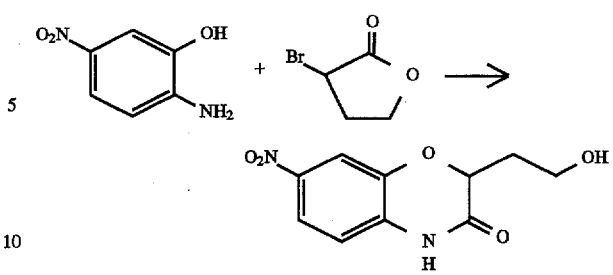

Method B: 5-nitro-2-aminophenol (13.5 g, 87.6 mmol, 1 eq.) and α-bromo-γ-butyrolactone (8.0 ml, 96.3 mmol, 1.1 eq.) were added to a stirring mixture of DMF (80 ml) and potassium carbonate (12.1 g, 87.6 mmol). After refluxing 5 hours and returning to room temperature, the reaction was poured into an equal volume of ice water and was stirred 15 minutes before being filtered. The resulting brown solid was dried in vacuo at 65° C. to afford a 45% yield of the product.

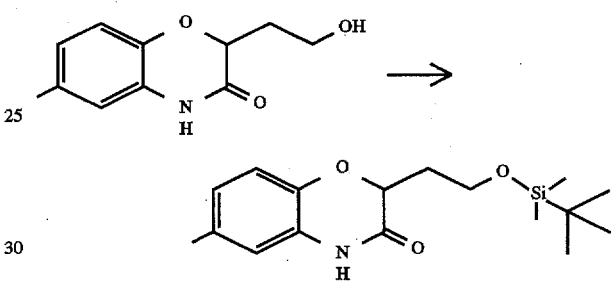

Method C: The 2-(2-hydroxyethyl)benzoxazine (1.6 g, 1 eq), was dissolved in DMF (4 ml) and treated, sequentially, with chloro t-butyldimethylsilane (1.4 g, 1.2 eq) and imidazole (1.3 g, 2.5 eq) while stirring in a nitrogen atmosphere. After 18 h, the reaction mixture was diluted with CH$_2$Cl$_2$ and washed with water. The organic layer was concentrated and the product isolated in 93% yield, as a white powder by crystallization from MeOH/water.

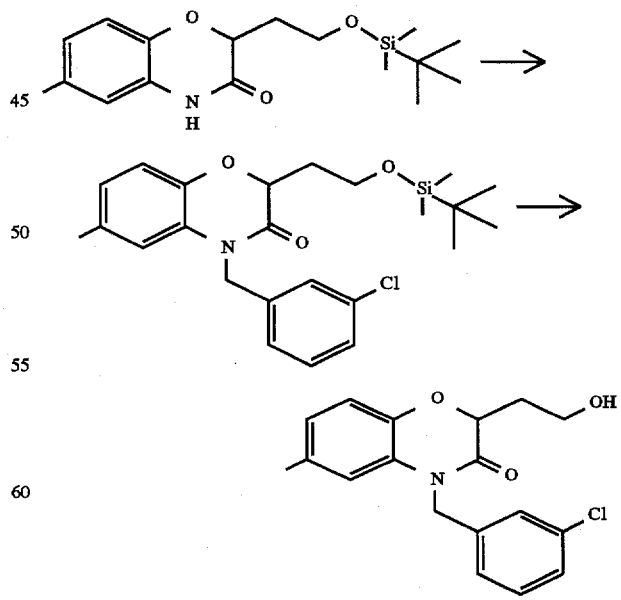

Method D: A solution of the silylated alcohol (2.17 g, 1 eq) in DMF (20 ml), was treated with NaH (60% oil dispersion, 0.27 mg, 1 eq) in one portion and stirred at room temperature in a nitrogen atmosphere for 20 min, followed by addition of 3-chloro-benzylbromide (0.89 ml, 1 eq). After 14 h, the crude reaction mixture was poured into cold water and extracted with EtOAc. The combined organic extract was washed with brine and concentrated under vacuum. The crude product was carried on to the next step without further purification.

Method E: The product from Method D was dissolved in THF (15 ml) and tetrabutylammonium fluoride (TBAF, 1M solution in THF, 13 ml, 2 eq) was added. After stirring at room temperature for 8 h, the reaction mixture was concentrated under vacuum. The crude product was subjected to flash chromatography, eluting with EtOAc, and additionally purified by trituration with hot hexanes to afford the product in 93% overall yield, as a white solid.

Method F: An alternative to the TBAF mediated desilylation procedure: The TBDMS-protected benzoxazine (3.1 mmol) was stirred into a milky mixture with AcOH (12 mL), THF (2 mL) and H$_2$O (5 mL). The resulting mixture was stirred for 18 h to give a clear solution. The addition of water gave a white solid precipitate which was filtered and dried in vacuo at 80° C.

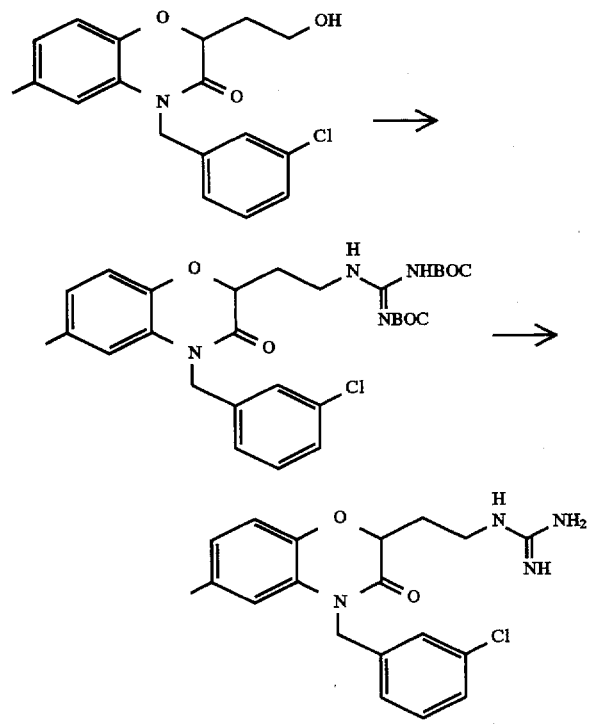

Method G: A solution of the benzoxazine alcohol (1.5 mmol), triphenylphosphine (2.3 mmol), and bis-BOC protected guanidine (3 mmol), in THF, was treated with DEAD (2.3 mmol). The reaction mixture was stirred overnight and concentrated under vacuum. Flash chromatography, eluting with EtOAc/Hexanes, afforded the product in sufficient purity to carry on to the deprotection step.

Method H: The protected guanidine intermediate was stirred overnight in 20 mL of 10% HCl/IPA, then concentrated under vacuum. The crude product was triturated with hot benzene, to remove impurities. Decantation afforded a semi-solid which could be triturated with Et$_2$O, filtered and added under vacuum.

Method I: The deprotection may also be carried out by stirring the protected guanidine overnight in 20 mL of 10% TFNCH$_2$Cl$_2$, then concentrating under vacuum.

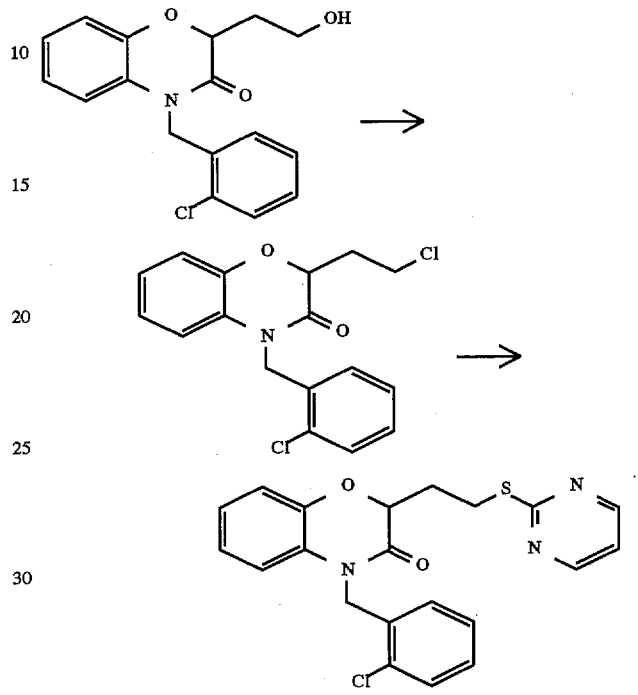

Method J: The benzoxazine alcohol (7.2 mmol) was dissolved in CCl$_4$ (25 mL) and trioctylphosphine (1.2 eq) was added slowly. The reaction mixture was stirred overnight and the solvent was evaporated under vacuum chromatography, eluting with EtOAc/hexanes, afforded the chloride.

Method K: The sodium salt of 2-mercaptopydmidine (5 eq, prepared by warming in 1N NaOH followed by evaporation of water) was dissolved in DMF and treated with the 2-chloroethylbenzoxazine derivative (1 eq). After stirring overnight, the reaction mixture was partitioned between Et$_2$O and water. The organic layer was washed with brine, added over MgSO$_4$ and concentrated under vacuum. Chromatography, eluting with EtOAc/hexanes, afforded the product.

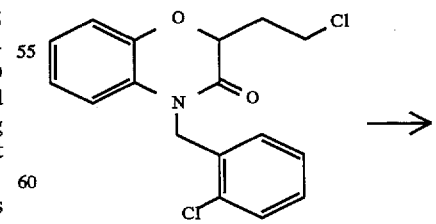

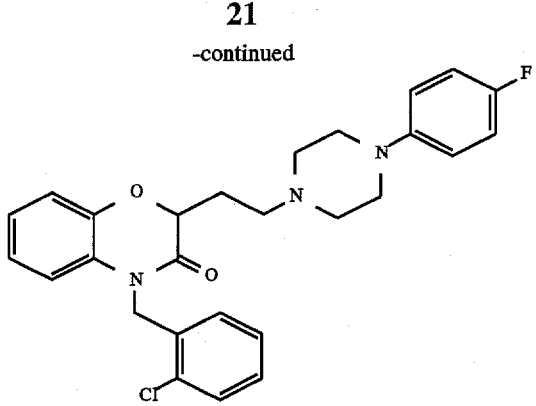

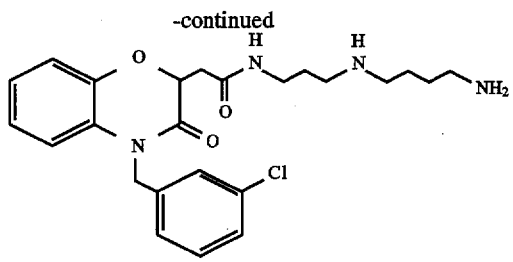

Method L: The 2-chloroethylbenzoxazine derivative (0.74 mmol) and 3 ml of 1-(4-fluorophenyl)piperazine were stirred overnight. The crude mixture was poured into ice-water and extracted with EtOAc. The organic layer was washed with brine, dried over $MgSO_4$ and the solvent evaporated under vacuum. The product could be purified by crystallization from $Et_2O$.

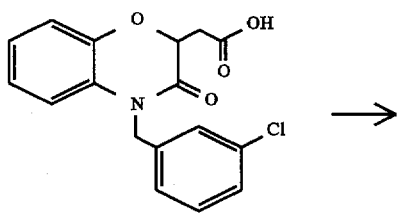

Method M: The benzoxazine carboxylic acid (1 eq) and the N',N''-diBOC-polyamine (1.1 eq)(R. Goodnow, et. al., *Tetrahedron* 1990, 46, 3267) were dissolved in $CH_2Cl_2$ and treated with 4-dimethylaminopyridine (1.04 eq). The resulting solution was cooled in an ice bath and treated with a $CH_2Cl_2$ solution of DCC (1.04 eq), then allowed to warm to RT. After stirring overnight, the solvent was evaporated under vacuum. The diBOC, amide was isolated as a light yellow viscous material in 46% yield (FAB mass spec shows MH+ at m/z=659). Without further purification this material was dissolved in isopropanol (IPA) and ether and treated with an excess of $HCl_{(g)}$ in IPA at rt for 18 h and at 50° C. for 2 h. The solvent was removed under vacuum and the residue was triturated with ether to afford the title compound as a beige solid in ~76% yield.

The following compounds were prepared according to the general procedures described above, as indicated, with the appropriate modifications in starting materials and reactants corresponding to the substituents indicated.

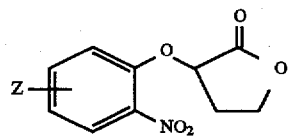

| Example | Z | Data | Method |
|---|---|---|---|
| 1 | H | $^1$H NMR ($CDCl_3$) δ 7.84 (dd, J=8.1, 1.6Hz, 1H), 7.62–7.48 (m, 2H), 7.16 (m, 1H), 5.02 (apparent t, J=7.4Hz, 1H), 4.62–4.52 (m, 1H), 4.45–4.35 (m, 1H), 2.83–2.55 (m, 3H) | A |
| 2 | 6-$CF_3$ | $^1$H NMR ($CDCl_3$) δ 2.63–2.86 (m, 2H), 4.40–4.48 (m, 1H), 4.58–4.65 (m, 1H), 5.14 (t, J=7.4Hz, 1H), 7.63 (d, J=8.8Hz, 1H), 7.83 (dd, J=8.8, 1.9Hz, 1H), 8.14 (d, J=1.9Hz, 1H) | A |
| 3 | 6-$CH_3$ | $^1$H NMR ($CDCl_3$) δ 7.66 (s, 1H), 7.38 (m, 2H), 4.93 (apparent t, J=7.4Hz, 1H), 4.59 (m, 1H), 4.39 (apparent q, J=7.3Hz, 1H), 2.78–2.61 (m, 2H), 2.38 (s, 3H) | A |

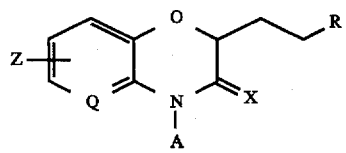

| Example | A | Z | X | Q | R | Data | Method |
|---|---|---|---|---|---|---|---|
| 4 | H | H | O | N | OH | $^1$H NMR ($CDCl_3$) δ 8.04 (dd, J=4.8, 1.5Hz, 1H), 7.42 (s, 1H), 7.37–7.18 (m, 4H), 6.96 (dd, J=7.9, 4.8Hz, 1H), 5.31 (s, 2H), 4.85 (dd, J=7.5, 5.4Hz, 1H), 3.90 (m, 2H), 2.35–2.16 (m, 2H), 2.04 (t, 5.6Hz, 1H) | B |
| 5 | H | 7-$NO_2$ | O | CH | OH | $^1$H NMR (DMSO-$d_6$) δ 11.32 (br s, 1H), 7.9 (dd, 1H, J=2.4, 8.7Hz), 7.79 (s, 1H), 7.05 (d, 1H, J=8.7Hz), 4.82 (dd, 1H, J=3.8, 9.0Hz), 4.70 (br s, 1H), 3.59 (m, 2H), 1.98 (m, 1H), 1.90 (m, 1H) | B |
| 6 | H | 6- | O | CH | OTBS | $^1$H NMR ($CDCl_3$) δ 8.27 (br s, 1H), 6.86 (d, J= | C |

-continued

| | | | | | | | |
|---|---|---|---|---|---|---|---|
| | | CH₃ | | | | 8.1Hz, 1H), 6.76 (dd, J=8.1, 1.7Hz, 1H), 6.61 (d, J=1.7Hz, 1H), 4.72, (dd, J=9.7, 3.7 Hz, 1H), 3.95–3.78 (m, 2H), 2.28 (s, 3H), 2.20 (m, 1H), 2.00 (m, 1H), 0.90 (s, 9H), 0.70 (s, 3H) | |
| 7 | H | 6-CF₃ | O | CH | OTBS | ¹H NMR (CDCl₃) δ 8.59 (br s, 1H), 7.25, (m, 1H), 7.06 (m, 2H), 4.85 (dd, J=9.2, 3.8Hz, 1H), 3.85 (m, 2H), 2.23 (m, 1H), 2.02 (m, 1H), 0.89 (s, 9H), 0.07 (s, 3H), 0.06 (s, 3H) | C |
| 8 | H | H | O | CH | OTBS | ¹H NMR (CDCl₃) δ 8.78 (br s, 1H), 6.89 (m, 3H), 6.75 (m, 1H), 4.68 (dd, J=11.2, 3.5Hz, 1H), 3.84–3.65 (m, 2H), 2.11 (m, 1H), 1.93 (m, 1H), 0.81 (s, 9H), 0.07 (s, 3H), 0.06 (s, 3H) | C |
| 9 | H | H | O | N | OTBS | ¹H NMR (CDCl₃) δ 8.04 (dd, J=4.8, 1.5Hz, 1H), 7.42 (s, 1H), 7.37–7.18 (m, 4H), 6.96 (dd, J=7.9, 4.8Hz, 1H), 5.31 (s, 2H), 4.85 (dd, J=7.5, 5.4Hz, 1H), 3.90 (m, 2H), 2.35–2.16 (m, 2H), 2.04 (t, 5.6Hz, 1H) | C |
| 10 | H | 7-NO₂ | O | CH | OTBS | ¹H NMR (DMSO-d₆) δ 8.17 (s, 1H), 8.13 (s, 1H), 7.86 (s, 1H), 7.83 (d, 1H, J=2.5Hz), 7.65 (d, 1H, J=7.8Hz), 7.58 (t, 1H, J=7.8Hz), 7.08 (d, 1H, J=9.2Hz), 5.40 (d, 1H, J=16.5 Hz), 5.31 (d, 1H, J=16.6), 5.07 (dd, 1H, J= 4.0, 9.0Hz), 4.57 (t, 1H, J=5.2Hz), 3.80 (m, 2H), 2.23 (m, 1H), 2.10 (m, 1H) | C |
| 11 | 3-ClBz | 6-CH₃ | O | CH | OH | ¹H NMR (CDCl₃) δ 7.27 (m, 3H), 7.17 (m, 1H), 6.90 (d, J=8.1Hz, 1H), 6.79 (d, J=7.0Hz, 1H), 6.63 (s, 1H), 5.17 (d, J=16.3Hz, 1H), 5.08 (d, J=16.3Hz, 1H), 4.80 (dd, J=7.6, 5.5 Hz, 1H), 3.92 (apparent q, J=5.8Hz, 2H), 2.29–2.17 (m, 3H), 2.23 (s, 3H) | D,E |
| 12 | 3-NO₂Bz | H | O | CH | OH | ¹H NMR (CDCl₃) δ 8.15 (s, 1H), 8.13 (s, 1H), 7.54 (m, 2H), 7.04 (m, 2H), 6.95 (m, 1H), 6.79 (d, 1H, J=7.6Hz), 5.28 (d, 1H, J=16.5Hz), 5.21 (d, 1H, J=16.5Hz), 4.90 (dd, 1H, J=5.5, 7.6Hz), 3.93 (m, 2H), 2.29 (m, 2H), 2.13 (t, 1H, J=5.6Hz) | D,F |
| 13 | 3-ClBz | H | O | N | OH | ¹H NMR (CDCl₃) δ 8.04 (dd, J=4.8, 1.5Hz, 1H), 7.42 (s, 1H), 7.37–7.18 (m, 4H), 6.96 (dd, J=7.9, 4.8Hz, 1H), 5.31 (s, 2H), 4.85 (dd, J=7.5, 5.4Hz, 1H), 3.90 (m, 2H), 2.35–2.16 (m, 2H), 2.04 (t, 5.6Hz, 1H) | D,E |
| 14 | 2-ClBz | H | O | CH | OH | ¹H NMR (CDCl₃) δ 7.42 (dd, J=7.6, 1.5Hz, 1H), 7.30–7.13 (m, 2H), 7.08–9.88 (m, 4H), 6.73 (dd, J=7.9, 1.3Hz, 1H), 5.25 (d, J=17.2 Hz, 1H), 5.23 (d, J=17.3Hz, 1H), 4.88 (dd, J=7.5, 5.5Hz, 1H), 3.95 (apparent q, J=5.9Hz, 2H), 2.40–2.20 (m, 2H), 2.19 (t, J=5.9Hz, 1H) | D,E |
| 15 | 3-ClBz | 6-CF₃ | O | CH | OH | ¹H NMR (CDCl₃) δ 2.20–2.40 (m, 2H), 3.92 (t, J=6.3Hz, 2H), 4.93 (t, J=7.6Hz, 1H), 5.14 (s, 2H), 7.07–7.16 (m, 3H), 7.23–7.30 (m, 4H) | D,E |
| 16 | 3-ClBz | H | O | CH | OH | ¹H NMR (CDCl₃) 7.26 (m, 1H), 7.12 (m, 1H), 7.01 (m, 2H), 6.94 (m, 1H), 6.82 (m, 1H), 5.15 (d, 1H, J=16.3Hz), 5.08 (d, 1H, J=16.2Hz), 4.85 (dd, 1H, J=5.5, 7.6Hz), 3.92 (d, 2H, J= 4.9Hz), 2.39–2.14 (br. m, 3H) | D,E |
| 17 | 3-ClBz | 7-NO₂ | O | CH | OH | ¹H NMR (DMSO-d₆) δ 7.94 (s, 1H), 7.92 (d, 1H, J=2.6Hz), 7.75 (br t, 1H), 7.40–6.85 (v br s, 4H), 7.38 (m, 3H), 7.21 (m, 2H), 5.30 (d, J= 16.7Hz, 1H), 5.17 (d, J=16.8Hz, 1H), 5.05 (dd, J=3.8, 9.5Hz, 1H), 3.42 (m, 2H), 2.22 (m, 1H), 2.08 (m, 1H) | D,E |
| 18 | 3-ClBz | 6-CF₃ | O | CH |  | ¹H NMR (DMSO-d₆) δ 7.71 (br t, J=6.4Hz, 1H), 7.5–6.9 (v br s, 4H), 7.38 (m, 4H), 7.25 (m, 3H), 5.32 (d, J=17.3Hz, 1H), 5.21 (d, J=17.3 Hz, 1H), | G,I |
| 19 | 3-ClBz | 6-CH₃ | O | CH |  | ¹H NMR (DMSO-d₆) δ 7.75 (br t, J=5.5Hz, 1H), 7.5–6.9 (v br s, 4H), 7.38 (m, 3H), 7.21 (d, J=8.5Hz, 1H), 6.98 (d, J=8.5Hz, 1H), 6.92 (s, 1H), 6.83 (d, J=8.5Hz, 1H), 5.2 (d, J=16.8 Hz, 1H), 5.09 (d, J=16.8Hz, 1H), 4.81 (dd, J= 9.2, 4.5Hz, 1H), 3.35 (m, 2H), 2.18 (s, 3H), 2.17 (m, 1H), 2.04 (m, 1H), 5.0 (dd, 10.0, 4.4 Hz, 1H), 3.34 (m, 2H), 2.21 (m, 1H), 2.1 (m, 1H) | G,H |

-continued

| # | R1 | R2 | X | Y | Substituent | ¹H NMR | Method |
|---|---|---|---|---|---|---|---|
| 20 | 3-ClBz | H | O | N | HN-C(=NH)-NH₂ | ¹H NMR (DMSO-d₆) δ 8.04 (dd, J=4.6, 1.9Hz, 1H), 7.72 (br t, J=5.5Hz, 1H), 7.2–6.85 (v br s, 4H), 7.5 (dd, J=9.1, 1.9Hz, 1H), 7.32 (m, 3H), 7.24 (d, J=7.3Hz, 1H), 7.12 (dd, J=9.1, 5.5 Hz, 1H), 5.25 (d, J=17.3Hz, 1H), 5.21 (d, J=17.3Hz, 1H), 4.98 (dsd, J=10.0, 3.9Hz, 1H), 3.39 (m, 2H), 2.20 (m, 1H), 2.07 (m, 1H) | G,H |
| 21 | 3-NO₂Bz | H | O | CH | HN-C(=NH)-NH₂ | ¹H NMR (DMSO-d₆) δ 8.17 (s, 1H), 8.13 (d, 1H, J=7.9Hz), 7.86 (br.t., 1H), 7.65 (m, 2H), 7.55–7.00 (br.s., 4H), 7.06 (m, 4H), 5.34 (d, 1H, J=16.7Hz), 5.27 (d, 1H, J=16.7Hz), 4.89 (dd, 1H, J=3.9, 9.0Hz), 3.38 (m, 2H), 2.21 (m, 1H), 2.07 (m, 1H) | G,H |
| 22 | 2-ClBz | H | O | CH | HN-C(=NH)-NH₂ | ¹NMR (DMSO-d₆) δ 7.89 (br t, 1H), 7.71–6.53 (v br s, 5H), 7.53 (d, 1H, J=7.2Hz), 7.30 (m, 2H), 7.13 (d, 1H, J=7.5Hz), 7.02 (m, 2H), 6.84 (d, 1H, J=7.2Hz), 5.21 (d, 1H, J=17.0Hz), 5.09 (d, 1H, J=17.4Hz), 4.91 (d, 1H, J=5.1Hz), 3.40 (m, 2H), 2.20 (m, 1H), 2.08 (m, 1H) | G,H |
| 23 | 3-ClBz | 7-NO₂ | O | CH | HN-C(=NH)-NH₂ | ¹H NMR (DMSO-d₆) δ 7.94 (s, 1H), 7.92 (d, 1H, J=2.6Hz), 7.75 (brt, 1H), 7.40–6.85 (vbrs, 4H), 7.38 (m, 3H), 7.21 (m, 2H), 5.30 (d, 1H, J=16.7Hz), 5.17 (d, 1H, J=16.8Hz), 5.05 (dd, 1H, J=3.8, 9.5Hz), 3.42 (m, 2H), 2.22 (m, 1H), 2.08 (m, 1H) | G,H |
| 24 | 2-ClBz | H | O | CH | (N-methyl-tetrazolyl)-S- | ¹H NMR (DMSO-d₆) δ 7.52 (d, J=7.3Hz, 1H), 7.28 (m, 2H), 7.10 (d, J=7.6Hz, 1H), 6.98 (m, 3H), 6.82 (d, J=6.8Hz, 1H), 5.19 (d, J=17.5 Hz, 1H), 5.09 (d, J=17.1Hz, 1H), 4.99 (dd, J=4.0, 8.4Hz, 1H), 3.93 (s, 3H), 3.51 (m, 2H), 2.45 (m, 1H), 2.31 (m, 1H) | J,K |
| 25 | 2-ClBz | H | O | CH | pyrrolidinyl-C(=S)-S- | ¹H NMR (CDCl₃) δ 7.41 (dd, J=2.1, 7.6Hz, 1H), 7.19 (m, 2H), 7.07 (dd, J=1.6, 7.9Hz, 1H), 6.98 (m, 1H), 6.91 (m, 2H), 6.70 (dd, J=1.3, 7.9Hz, 1H), 5.25 (d, J=17.1Hz, 1H), 5.17 (d, 1H, J=17.1Hz), 4.83 (dd, J=4.3, 9.3Hz, 1H), 3.93 (t, J=6.9Hz, 2H), 3.66 (m, 2H), 3.54 (m, 2H), 2.47 (m, 1H), 2.33 (m, 1H), 2.09 (m, 2H), 1.97 (m, 2H) | J,K |
| 26 | 2-ClBz | H | O | CH | pyrimidin-2-yl-S- | ¹H NMR (CDCl₃) δ 8.50 (d, 2H, J=4.8Hz), 7.41 (dd, J=1.7, 7.7Hz, 1H), 7.18 (m, 2H), 6.99 (m, 5H), 6.70 (dd, J=1.3, 7.9Hz, 1H), 5.22 (s, 2H), 4.91 (dd, J=3.9, 9.6Hz, 1H), 3.52 (m, 1H), 3.34 (m, 1H), 2.53 (m, 1H), 2.39 (m, 1H) | J,K |
| 27 | 2-ClBz | H | O | CH | 4-benzylpiperazin-1-yl | ¹H NMR (CDCl₃) δ 7.41 (d, J=7.7Hz, 1H), 7.26 (m, 7H), 6.90 (m, 4H), 6.67 (d, J=7.8Hz, 1H), 5.23 (d, J=17.1Hz, 1H), 5.19 (d, J=17.1 Hz, 1H), 4.82 (dd, J=4.1, 8.9Hz 1H), 3.50 (s, 2H), 2.62 (m, 2H), 2.49 (br s, 8H), 2.18 (m, 1H), 2.08 (m, 1H) | J,L |
| 28 | 2-ClBz | H | O | CH | 4-(4-fluorophenyl)piperazin-1-yl | ¹H NMR (CDCl₃) δ 7.42 (d, J=7.7Hz, 1H), 7.18 (m, 2H), 6.94 (m, 8H), 6.70 (d, J=7.8Hz, 1H), 5.22 (s, 2H), 4.86 (dd, J=4.1, 8.7Hz, 1H), 3.12 (t, J=4.7Hz, 4H), 2.67 (m, 6H), 2.22 (m, 1H), 2.14 (m, 1H) | J,L |
| 29 | 3-ClBz | H | O | CH | HN(CHO)-(CH₂)₃-NH-(CH₂)₄-NH₂ | ¹H NMR (DMSO-d₆) δ 1.56–1.75 (m, 4H), 1.75–1.89 (m, 2H), 2.73–2.94 (m, 8H), 3.14–3.22 (m, 2H), 5.10–5.24 (m, 3H), 6.92–7.04 (m, 4H), 7.23–7.43 (m, 4H), 8.08 (br s, 3H), 8.35 (t, J=6.5Hz, 1H), 9.03 (br s, 2H) | M |

We claim:

1. A method of treating bacterial infections in mammals by administering to a mammal suffering from such infection a therapeutically effective amount of a compound selected from those of Formula 1:

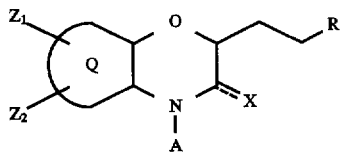

wherein the moiety Q is a fused phenyl moiety;

$Z_1$ is hydrogen, halogen, $C_1$–$C_6$alkyl, $C_1$–$C_6$alkoxy, phenyl, hydroxy, amino, nitro, sulfonylamino or trifluoromethyl;

$Z_2$ is hydrogen or a halogen;

X is hydrogen or oxygen;

A is —$C_1$–$C_6$alkyl, —$C_1$–$C_6$alkylaryl or —$C_1$–$C_6$ alkylheterocyclyl where in each case the A moiety is bonded to the nitrogen through the alkyl group;

wherein aryl is biphenyl, naphthyl or phenyl; and heterocyclyl is a 5 or 6 membered saturated or unsaturated heterocyclic group containing 1–4 nitrogen atoms and/or an oxygen or a sulfur atom;

wherein said aryl or heterocyclyl group is optionally substituted with ($C_1$–$C_6$)alkyl, benzyl, oxybenzyl, phenoxy, hydroxy, alkoxy, halogen, dihalogen, nitro, amino, carboxyl, carbo($C_1$–$C_4$)alkoxy or methylsulfonylamino;

R is a moiety selected from:

(a) $NR_1R_2$, $N^+R_1R_2R_3$; or (b) 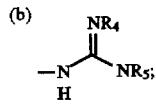

wherein $R_1$, $R_2$ and $R_3$ are independently hydrogen, $C_1$–$C_6$alkyl, t-butoxycarbonyl, or carboxyethylpiperidine;

$R_4$ and $R_5$ are independently t-butoxycarbonyl or hydrogen or $R_4$ and $R_5$ may be joined together to form an imidazoline, imidazolyl or pyrimidine ring;

and the pharmaceutically acceptable salts, esters and prodrug forms thereof.

2. A method according to claim 1 wherein the moiety A is selected from $C_1$–$C_5$ alkyl, $CH_2$phenyl, $CH_2$thienyl, $CH_2$pyridyl, $CH_2$furyl, and ethyl piperidine.

3. A method according to claim 1 wherein:

the moiety Q is fused phenyl;

$Z_1$ is hydrogen, halogen, $C_1$–$C_6$alkyl, $C_1$–$C_6$alkoxy, phenyl, hydroxy, amino, nitro, sulfonylamino or trifluoromethyl;

$Z_2$ is hydrogen or, where $Z_1$ is a halogen, $Z_2$ is also a halogen;

X is oxygen;

A is $C_1$–$C_5$alkyl, —$CH_2$phenyl, —$CH_2$thienyl, —$CH_2$pyridyl, —$CH_2$furyl, or -ethyl piperidine; wherein said phenyl, thienyl, pyridyl, furyl or piperidine moiety is optionally substituted with ($C_1$–$C_6$) alkyl, benzyl, oxybenzyl, phenoxy, hydroxy, alkoxy, halogen, dihalogen, nitro, amino, carboxyl or carbomethoxy;

R is the moiety:

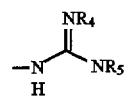

wherein $R_4$ and $R_5$ are independently t-butoxycarbonyl or hydrogen or $R_4$ and $R_5$ may be joined together to form an imidazoline, imidazolyl or pyrimidine ring;

and the pharmaceutically acceptable salts, esters and prodrug forms thereof.

4. A compound for treating bacterial infections in mammals selected from those of Formula 1:

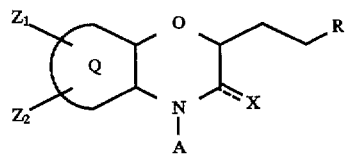

wherein the moiety Q is fused phenyl;

$Z_1$ is hydrogen, halogen, $C_1$–$C_6$alkyl, $C_1$–$C_6$alkoxy, phenyl, hydroxy, amino, nitro, sulfonylamino or trifluoromethyl;

$Z_2$ is hydrogen or, where $Z_1$ is a halogen, $Z_2$ is also a halogen;

X is oxygen;

A is $C_1$–$C_5$alkyl, —$CH_2$phenyl, —$CH_2$thienyl, —$CH_2$pyridyl, —$CH_2$furyl, or -ethyl piperidine; wherein said phenyl, thienyl, pyridyl, furyl or piperidine moiety is optionally substituted with ($C_1$–$C_6$) alkyl, benzyl, oxybenzyl, phenoxy, hydroxy, alkoxy, halogen, dihalogen, nitro, amino, carboxyl or carbomethoxy;

R is the moiety:

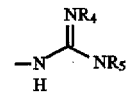

wherein $R_4$ and $R_5$ are independently t-butoxycarbonyl or hydrogen or $R_4$ and $R_5$ may be joined together to form an imidazoline, imidazolyl or pyrimidine ring;

and the pharmaceutically acceptable salts, esters and prodrug forms thereof.

5. The compound according to claim 4 wherein:

Q is a fused phenyl moiety; $Z_1$ is 6-trifluoromethyl; $Z_2$ is hydrogen; X is oxygen; A is 3-chlorobenzyl; and R is guanidino.

6. The compound according to claim 4 wherein:

Q is a fused phenyl moiety; $Z_1$ is 6-methyl; $Z_2$ is hydrogen; X is oxygen; A is 3-chlorobenzyl; and R is guanidino.

7. The compound according to claim 4 wherein:

Q is a fused phenyl moiety; $Z_1$ is hydrogen; $Z_2$ is hydrogen; X is oxygen; A is 3-nitrobenzyl; and R is guanidino.

8. The compound according to claim 4 wherein:

Q is a fused phenyl moiety; $Z_1$ is hydrogen; $Z_2$ is hydrogen; X is oxygen; A is 2-chlorobenzyl; and R is guanidino.

9. The compound according to claim 4 wherein:

Q is a fused phenyl moiety; $Z_1$ is 7-nitro; $Z_2$ is hydrogen; X is oxygen; A is 3-chlorobenzyl; and R is guanidino.

10. A pharmaceutical composition for treating bacterial infections comprising an effective amount of a compound selected from claim 4 in association with a pharmaceutically acceptable carrier.

11. A method of potentiating the activity of an antibacterial agent in mammals by administering said antibacterial agent in combination with a compound selected from claim 4.

12. A pharmaceutical composition for treating bacterial infections comprising an antibacterial agent and a compound selected from claim 4 in therapeutically effective amounts in association with a pharmaceutically acceptable carrier.

13. A method of preparing a compound selected from those of Formula 1:

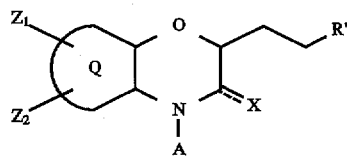

wherein the moiety Q is a fused phenyl moiety;

$Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or, where $Z_1$ is a halogen, $Z_2$ is also a halogen;

X is oxygen;

A is $C_1$–$C_5$ alkyl, —$CH_2$phenyl, —$CH_2$thienyl, —$CH_2$pyridyl, —$CH_2$furyl, or -ethyl piperidine; wherein said phenyl, thienyl, pyridyl, furyl or piperidine moiety is optionally substituted with ($C_1$–$C_6$) alkyl, benzyl, oxybenzyl, phenoxy, hydroxy, alkoxy, halogen, dihalogen, nitro, amino, carboxyl or carbomethoxy;

R' is a moiety;

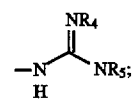

wherein $R_4$ and $R_5$ are independently t-butoxycarbonyl or hydrogen or $R_4$ and $R_5$ may be joined together to form an imidazoline, imidazolyl or pyrimidine ring; and the pharmaceutically acceptable salts, esters and pro-drug forms thereof, which comprises reacting a compound of the formula:

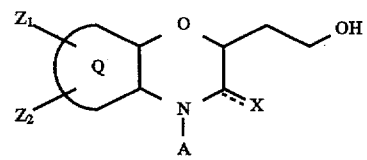

with a halogenating agent to form a halogenated compound of the formula:

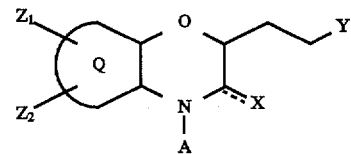

wherein the moiety Y is a halogen, in a suitable solvent followed by reacting said halogenated compound with compound of the formula HR' wherein R' is as hereinbefore defined and recovering the compound of formula 1.

* * * * *